US011259606B2

(12) United States Patent
Dencek

(10) Patent No.: US 11,259,606 B2
(45) Date of Patent: Mar. 1, 2022

(54) TECHNICIAN'S CORD POSITIONER

(71) Applicant: Debra M Dencek, Cave Creek, AZ (US)

(72) Inventor: Debra M Dencek, Cave Creek, AZ (US)

(*) Notice: Subject to any disclaimer, the term of this patent is extended or adjusted under 35 U.S.C. 154(b) by 404 days.

(21) Appl. No.: 15/823,544

(22) Filed: Nov. 27, 2017

(65) Prior Publication Data

US 2018/0343985 A1 Dec. 6, 2018

Related U.S. Application Data

(63) Continuation-in-part of application No. 29/605,921, filed on May 31, 2017, now Pat. No. Des. 859,237.

(51) Int. Cl.
| | |
|---|---|
| *A44C 5/00* | (2006.01) |
| *A61B 90/53* | (2016.01) |
| *A61C 3/04* | (2006.01) |
| *H02G 11/00* | (2006.01) |
| *A61C 19/00* | (2006.01) |
| *A61C 3/00* | (2006.01) |
| *H02G 3/32* | (2006.01) |

(52) U.S. Cl.
CPC ............ *A44C 5/0007* (2013.01); *A61B 90/53* (2016.02); *A61C 3/04* (2013.01); *A61C 19/00* (2013.01); *H02G 11/00* (2013.01); *A61C 3/00* (2013.01); *H02G 3/32* (2013.01)

(58) Field of Classification Search
CPC ........... A44C 5/007; A61B 90/53; A61C 3/04; A45F 2005/008
See application file for complete search history.

(56) References Cited

U.S. PATENT DOCUMENTS

| | | | |
|---|---|---|---|
| D39,960 S | 5/1909 | Mussillon | |
| 1,544,386 A | 6/1925 | Fridolph | |
| 2,373,328 A | 4/1945 | Morehouse | |
| 2,871,592 A | 2/1959 | Polzin | |
| 3,285,243 A * | 11/1966 | Yellin | ............ A61F 5/055 |
| | | | 602/18 |
| D259,242 S | 5/1981 | Gilb | |
| 4,957,232 A | 9/1990 | Sprague | |
| 5,024,402 A | 6/1991 | Hamel | |
| D353,990 S | 1/1995 | Alfreds | |
| 5,517,838 A | 5/1996 | Moore | |
| 5,802,676 A | 9/1998 | Tolan | |
| 5,845,374 A | 12/1998 | Briggs | |
| 6,085,393 A | 7/2000 | Tsui | |
| 6,092,444 A | 7/2000 | Hsiao | |
| 6,131,200 A | 10/2000 | McNamara | |

(Continued)

*Primary Examiner* — Victor D Batson
*Assistant Examiner* — Matthew J Sullivan
(74) *Attorney, Agent, or Firm* — Scott A. Hill; The Hill Law Firm, PLC

(57) ABSTRACT

Positioning a cord of a corded instrument is accomplished by securing a wearable cord positioner around a wrist or arm of a technician, and then pressing a cord into the cord positioner. A body of the cord positioner holds the cord in a substantially fixed position relative to a band. The body may be fixed relative to the band, or the body may be adjustable such that the cord can enter and exit the body at different angles relative to the band. The body may be removeably fastened to the band for easy cleaning or to change the body with a body designed to hold and position a different sized of cord.

20 Claims, 3 Drawing Sheets

(56) References Cited

U.S. PATENT DOCUMENTS

| | | |
|---|---|---|
| 6,279,804 B1 | 8/2001 | Gregg |
| 6,467,132 B1 | 10/2002 | Robley |
| 6,490,767 B2 | 12/2002 | Haiduk |
| 6,523,229 B2 | 2/2003 | Severson |
| 6,581,885 B2 | 6/2003 | Polad |
| 6,676,674 B1 | 1/2004 | Dudai |
| 6,701,580 B1 | 3/2004 | Bandyopadhyay |
| 6,763,554 B1 | 7/2004 | Torrey |
| D495,972 S | 9/2004 | Petingill |
| D505,785 S | 6/2005 | Woody |
| D511,450 S | 11/2005 | Seth |
| 7,013,492 B2 * | 3/2006 | Hugh .................. H04R 1/1016 2/243.1 |
| 7,039,958 B2 | 5/2006 | Henricksen |
| 7,096,544 B2 | 8/2006 | Lusardi |
| D543,833 S | 6/2007 | Folk |
| 7,252,450 B2 | 8/2007 | Aguirre et al. |
| 7,356,888 B2 | 4/2008 | Chao |
| 7,624,480 B2 | 12/2009 | Coronel |
| 7,731,069 B2 | 6/2010 | Lopreiato |
| D629,286 S * | 12/2010 | Laskowski ..................... D8/356 |
| D652,756 S | 1/2012 | Lans |
| D660,740 S | 5/2012 | Cullen |
| D662,087 S | 6/2012 | Peller |
| D666,076 S | 8/2012 | Muratore |
| D667,043 S | 9/2012 | Couch, III |
| D675,123 S | 1/2013 | Nunez |
| 8,413,306 B2 | 4/2013 | Gallant |
| 8,458,864 B1 | 6/2013 | Patton |
| D691,910 S * | 10/2013 | Kelleghan ..................... D11/216 |
| D693,992 S | 11/2013 | Dinunzio |
| D712,295 S | 9/2014 | Ennis et al. |
| D729,045 S | 5/2015 | Cavanaugh |
| D732,933 S | 6/2015 | Jansen |
| D733,525 S | 7/2015 | Petzl |
| D739,974 S * | 9/2015 | Kelleghan ..................... D11/201 |
| D740,106 S | 10/2015 | Cooper |
| 9,340,341 B2 | 5/2016 | Farrell |
| 9,550,550 B1 | 1/2017 | Housman |
| D794,490 S | 8/2017 | Lindgren |
| 9,901,148 B2 * | 2/2018 | Steve ................... A44C 5/2076 |
| D811,859 S | 3/2018 | Orser |
| D813,016 S | 3/2018 | Deneau |
| D867,922 S * | 11/2019 | Steve ........................ D11/216 |
| 2001/0013277 A1 | 8/2001 | Galkiewicz |
| 2002/0020045 A1 * | 2/2002 | Nasu ....................... A45F 5/02 24/546 |
| 2003/0110596 A1 | 6/2003 | Graham |
| 2003/0167605 A1 | 9/2003 | Schultz |
| 2004/0003487 A1 | 1/2004 | Reiter |
| 2004/0167456 A1 | 8/2004 | Kingsford |
| 2005/0251967 A1 | 11/2005 | McNeill |
| 2006/0032032 A1 | 2/2006 | Cheng |
| 2009/0106948 A1 | 4/2009 | Lopez |
| 2011/0010894 A1 * | 1/2011 | Honeycutt ........... A44C 15/003 24/3.1 |
| 2012/0018250 A1 | 1/2012 | Smith |
| 2013/0334385 A1 | 12/2013 | Steck |
| 2014/0090873 A1 * | 4/2014 | Metras .................. H01R 13/60 174/135 |
| 2014/0182087 A1 | 7/2014 | St. Jean |
| 2014/0262864 A1 | 9/2014 | Rothbaum |
| 2017/0095067 A1 * | 4/2017 | Duddy ..................... A45F 5/02 |
| 2017/0246632 A1 | 8/2017 | Slepian |

* cited by examiner

02 Cord positioner
10 Band
12 Loop-end
14 Loop
16 Adjustment holes
18 Connector end
20 Snap connector
22 Rivet
24 Body
26 Side
28 Raised portion
30 Base
32 Opening
34 Cord-holding portion
36 Relief
38 Channel
40 Buttress
42 Fastener

US 11,259,606 B2

TECHNICIAN'S CORD POSITIONER

BACKGROUND OF THE INVENTION

Dental instruments used to perform dental procedures are usually powered by a power source that is connected to the dental instrument using some sort of flexible cord. Air and electricity are common power sources.

While performing a procedure, the cord of a dental instrument frequently needs to be moved out of the way of a work area so that a dental technician can clearly see and perform their work. In order to maintain sanitary conditions between patients, most of the various instruments and tools used for a dental procedure are either thoroughly cleaned or discarded and replaced. Dental technicians try to avoid touching a cord before or after touching a patient's mouth, but it sometimes becomes necessary to position a cord away from a patient's face while trying to position a corded dental instrument.

SUMMARY OF THE INVENTION

The present invention is a cord positioner that provides a sanitary method for a cord to be positioned by a dental technician's arm such that the technician can maneuver the cord without touching the cord with a hand. An easy to wipe down band with a cord holder portion is worn by the technician, preferably around a wrist of the technician. The cord positioner is designed to be used with a particular range of cord diameters, so larger or smaller cords would require separate cord positioners. In a preferred embodiment, the cord positioner is molded as part of a flexible band so that there are few cracks or crevices that might be difficult to clean. The cord holder portion includes structure that helps a base resist bending and twisting a lot more than the rest of the band. In an alternate embodiment, any hard-to-clean surfaces and crevices are designed into disposable clip to minimize the time it takes to sanitize instruments and tools that are not disposable. Other types of technicians, such as tattoo artists, may find the present cord positioner to be useful.

The falling are the callouts used in FIGS. 1-12: 02 Cord positioner; 10 Band; 12 Loop-end; 14 Loop; 16 Adjustment holes; 18 Connector end; 20 Snap connector; 22 Rivet; 24 Body; 26 Side; 28 Raised portion; 30 Base; 32 Opening; 34 Cord-holding portion; 36 Relief; 38 Channel; 40 Buttress; 42 Fastener.

DETAILED DESCRIPTION OF THE INVENTION

Throughout this description, unless otherwise stated or shown, a cord positioner has two sides that are mirror images of each other when the apparatus is longitudinally bisected, so use of the plural for a single callout or feature is intended to describe both sides of the cord positioner in substantially the same way. Use of the same callout from drawing to drawing is intended to mean the same feature from a functional perspective even if features from drawing to drawing are not identical. The most preferred embodiment of the present invention, shown in FIGS. 1-5, is a cord positioner 2 characterized by a band 10 that has a centrally located body 24 that surrounds a channel 38. The body includes structures that allow a cord to be quickly and easily pressed into the channel such that the cord is attached to a technician's wrist or arm for easy manipulation of the cord without needing to grasp the chord with a free hand. The wearable band preferably includes an aesthetic design that is comfortable to wear. The cord holder portion is preferably made from a flexible plastic material that is inexpensive to manufacture. The cord holder portion is easy to manipulate so that it accepts a cord, and it is resilient such that it closes around the cord so that the cord is held in a desired alignment by the cord holder portion. In an alternate embodiment, the band and the cord holder portion are separate piece parts that fasten or clip together, and the cord holder portion is disposable or may be autoclaved.

The band can be a simple band or strap of material that wraps around a technician's arm, preferable near the wrist or elbow of the arm that is holding a corded instrument. A watch could be incorporated into the band, noting that it might be more difficult to clean. The preferred band is molded plastic, such as TPU, but the band can be substantially similar to any of the various watch bands or bracelets that offer comfort and support to a wearer. The band could also be an adhesively joined strip of Tyvek, similar to what is commonly used as a hospital identification band; or the band could be an adjustable vinyl or poly band, similar to what is commonly used as a medical alert bracelet, or the band could be magnetic. It is preferred that the band is somewhat flexible, yet the band should provide resistance to normal stresses that could unfasten the cord positioner. The term "band" is meant to include any type of bracelet, arm band, wrist-watch band or similar device.

Figure 1:
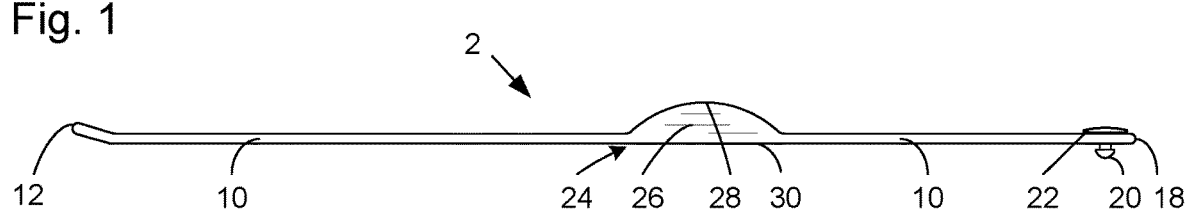
FIG. 1 is a side view of a cord positioner of the present invention.
Figure 2:
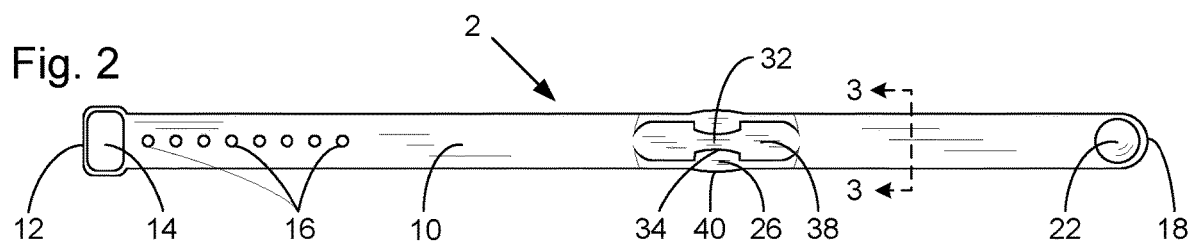
FIG. 2 is a plan view of the cord positioner of FIG. 1.

FIGS. 1 and 2 show a cord positioner 2 having a band 10 that straps around the wrist of a technician. The band has a loop-end 12 with a loop 14 and adjustable holes 16, similar to a common waist belt's construction. At the opposite end, the band has a connector end 18 with a snap connector 20 and a rivet 22. The connector end is wrapped around a technician's wrist so that the connector end can be passed through the loop of the loop end until the rivet can be lined up with a desired adjustment hole and the band can be snapped together to secure it to the wrist of the technician. Other common ways of attaching a band around someone's wrist or arm may be employed, such as the various constructions of watch bands, including snaps and hook and loop fasteners.

Somewhat centrally located on the band is the body 24 of the cord positioner 2. The body should be less flexible than the band, which may be accomplished by adding structure to the body, such as sides 26 that are raised relative to the otherwise flat band. The band preferably has s thickness of about 2 to 3 mm if it is to be attached around a wrist. The band shown in FIGS. 1-5, which is constructed to hold and position up to nominally sized 8 mm cords, is ideally about 13 mm wide, except that the loop end 12 and the body 24 should be wider. The term cord is intended to include hoses that carry air or water, as well as electrical cords. The overall length of the band, from connector end to loop end, is shown as being about 230 mm. The length of the band could be varied to accommodate wrist sizes that are smaller, or additional adjustment holes could be added to the band. For larger wrists sizes, a longer band would need to be constructed, such as 280 mm or longer.

The sides 26 of the body 24 are preferably their highest at raised portion 28, as shown in FIG. 1. The base 30 of the body 24 is fairly continuous with the band, but it is slightly wider to accommodate buttresses 40 on either side of the body. A cord positioner that accepts 8 mm cord is preferably about 9 mm high at the raised side portions 28. When considering that the base is a couple of millimeters thick, this means that it is intentional that an 8 mm cord will not fit inside channel 38 of the base without at least slightly pushing apart opening 32 as compared to a relaxed state where there is no cord installed in the cord positioner.

Figure 3:
FIG. 3 is a cross-sectional view through line 3-3 of FIG. 2.
Figure 4:
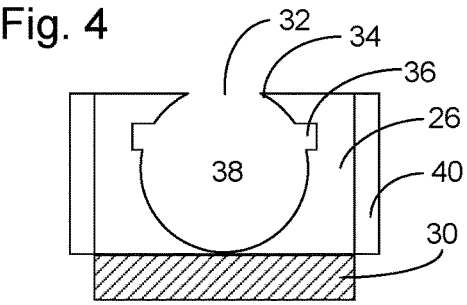
FIG. 4 is an enlarged view of FIG. 3.

Cord holder portions 34, most clearly seen in FIG. 4, which is an enlarged view of FIG. 3, which is a cross sectional view through line 3-3 of FIG. 2, are resilient and biased to pinch together at the opening 32. To allow for the opening to more easily expand when installing a cord into channel 38, reliefs 36 are provided, and buttresses 40 strengthen sides 26. Although the body could be constructed without buttresses or reliefs, these extra features seem to help with quality control when molding the cord positioner from plastic, such as TPU.

Installation of a cord into the channel is preferably accomplished when a user presses the cord of a corded instrument against the opening 32 in the body 24 of the cord positioner 2 until the cord-holder portions 34 spread apart enough to allow the cord to drop into channel 38. It is expected that a cord will deform a little bit during this process. Installation of the cord may be done when a technician is not wearing the cord positioner, but the preference is for a user to be wearing the cord positioner when pressing a cord into the channel. This means that the process should be relatively easy and capable of being performed with one free hand that grasps the cord and presses it into the opening 32. A technician may wiggle, roll and twist the cord against the cord holder portions a little to make this process easier. When the cord is installed into the cord positioner, most technicians will prefer that the instrument end of the cord is nearest the radial aspect of the technician's wrist, and a power supply end of the cord enters the cord positioner near the ulnar aspect of the technician's wrist. This is particularly true for corded instruments that are held like a writing instrument.

Figure 5:
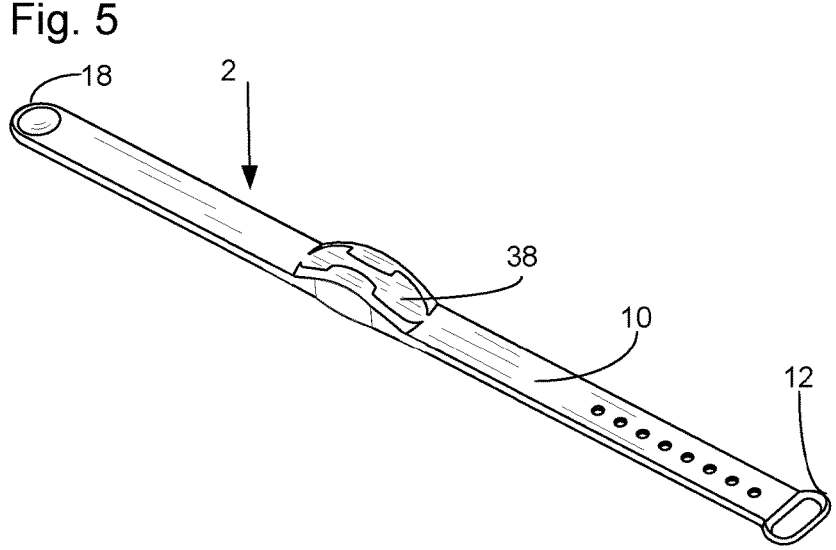
FIG. 5 is a perspective view of the cord positioner of FIGS. 1-4.

Smaller cords, such as 5 mm, may be used in a cord positioner designed for a larger cord, such as 8 mm. Because a smaller diameter cord is much lighter and usually more flexible, it is relatively secure within the channel 38, meaning that the cord holder portions aren't as likely to separate under the relatively small force exerted by any manipulations of a smaller cord when a technician maneuvers their wrist holding the cord positioner for the purpose of positioning themselves to use the instrument without being annoyed or inconvenienced by the cord, or to manipulate the cord away from someone on whom a procedure is being performed. At it's narrowest, the opening is about 2.5 mm wide from the cord holder portions on either side of the body. As shown in FIGS. 2 and 5, the opening is narrowest at a midpoint of the body because the width of the opening is tapered toward the midpoint. This allows a cord to be gradually less supported as it is farther from the midpoint to cause a more gradual bend of the cord when it is manipulated. A much smaller diameter cord than channel will allow the cord to slip back and forth through the channel. A sleeve may be added to a smaller diameter cord to reduce this slipping. Simply wrapping tape around a cord at a preferred length until it has a desired thickness is another method to reduce slipping.

Figure 6:
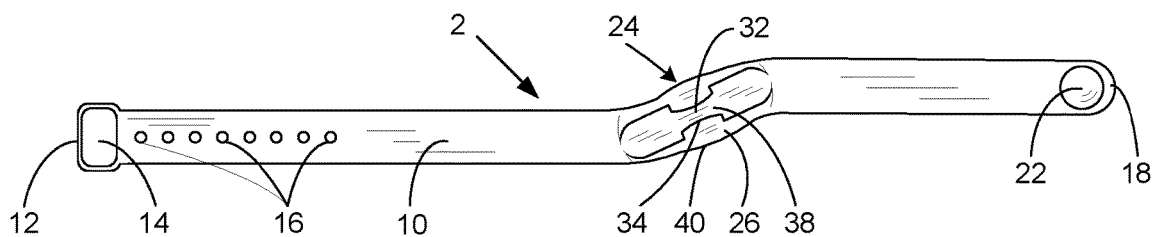
FIG. 6 is a plan view of an alternate alignment of the body of the cord positioner of FIGS. 1-5.

As shown in FIG. 6, the channel 38 of the cord positioner 2 can be aligned at an angle, such as but not limited to 30 or 45 degrees, relative to the band so that a cord in the cord positioner exits more in line with a desired position for use of a corded instrument. The orientation of FIG. 6 would tend to direct a cord toward the thumb if used on the left hand of a technician. The power source end of the cord would then be closer to the technician's left elbow. FIG. 6 shows that there is an offset of the band 10 that occurs because the body 24 is no longer aligned with the band, but the loop-end 12 of the band and the connector end of the band still are able to be joined in a normal fashion.

Figure 7:
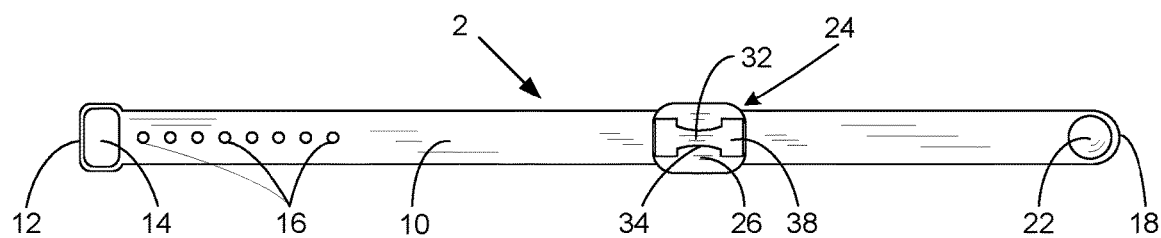
FIG. 7 is a plan view of an alternate embodiment of the present invention.
Figure 8:
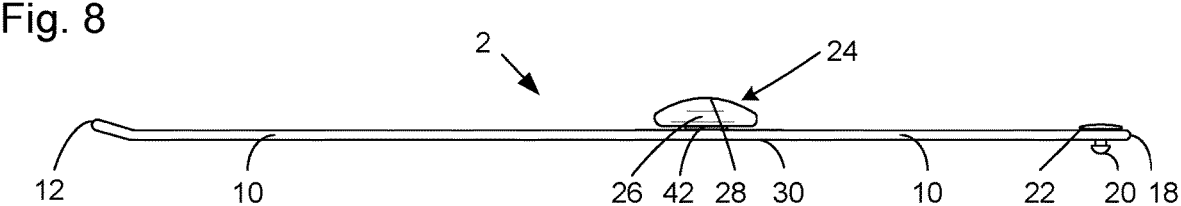
FIG. 8 is a side view of the cord positioner of FIG. 7.
Figure 9:
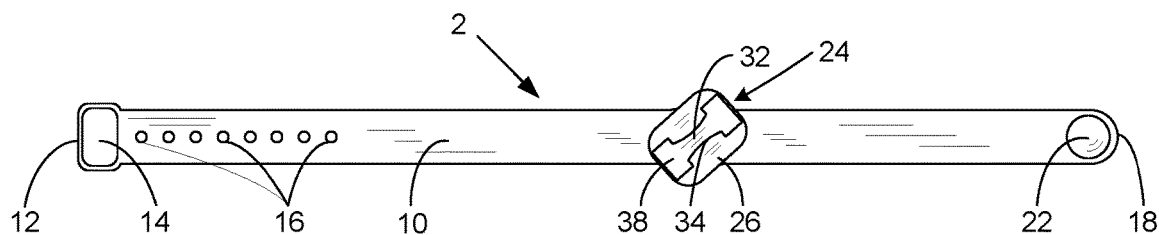
FIG. 9 is a plan view of the cord positioner of FIG. 7, but in an alternate configuration.

FIGS. 7-9 show an alternate embodiment of the present invention wherein the body 24 of the cord positioner 2 is a separate piece part from the band 10. The band is continuous from the loop-end 12 to the connector end 18, except that there is a fastener 42 near a midpoint of the band. This fastener fastens the band to the body, preferably such that the body may be rotated relative to the band. FIG. 9 shows the body rotated relative to the band such that the channel 38 is at about a 45 degree angle relative to the band. The body may be removable and interchangeable with another body that accommodates a different diameter cord. Making the body removable also makes it easier to clean the body and/or autoclave the body. The band may be simply wiped down.

Where the body and band are fastened to each other using a fastener, the fastener may be a snap, clasp, hook, magnet or button. A snap or button would allow the clip to rotate relative to the strap. A detent can be incorporated into the fastener itself, such as into a button or snap, or a detent can be incorporated into the clip and strap such that when they are rotated relative to each other the detent disengages and engages until a desired position is selected. The clip and strap can be fastened to each other by incorporating a structure similar to a nylon plug, rivet or pin, with a preference that the hole for receiving the fastener be in the strap. If using a magnet, the band may be made from a metallic material, and the body can have a permanent magnet insert molded into it, or a magnet can be insert molded into the band. Detents are preferably added so that the body 24 can be aligned with either the left thumb or right thumb of a technician. Detents about every 15 degrees would provide a lot of options for a user, noting that the cord used with a cord positioner is usually quite flexible.

Figure 10:
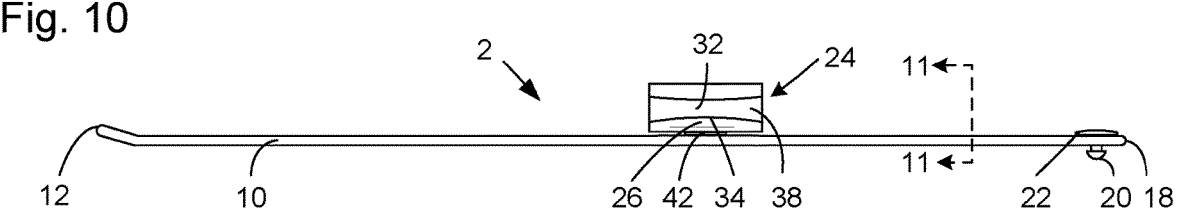
FIG. 10 is a side view of another alternate embodiment of the present invention.
Figure 11:
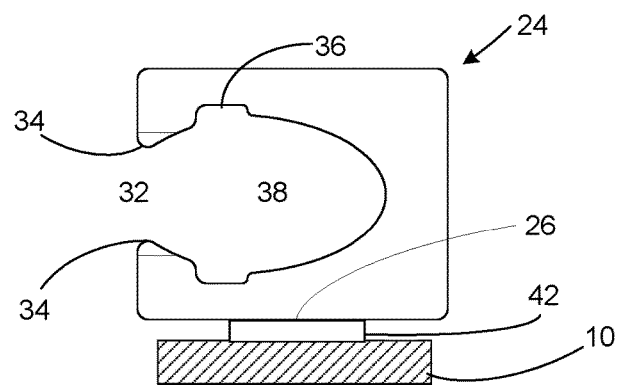
FIG. 11 is an enlarged cross-sectional view through line 11-11 of FIG. 10.
Figure 12:
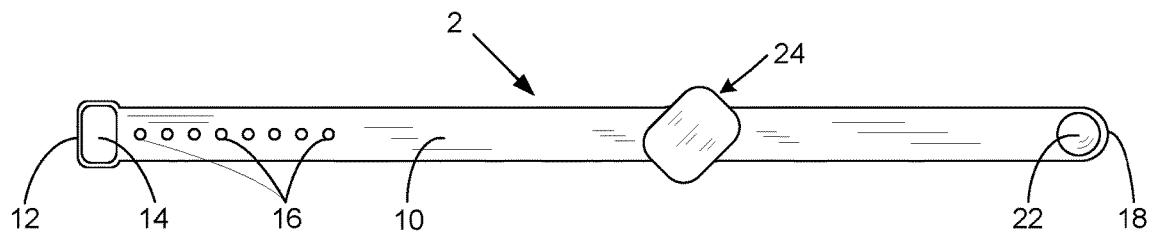
FIG. 12 is a plan view of the cord positioner of FIG. 10, but in an alternate configuration.

Yet another alternate embodiment of the present invention is shown in FIGS. 10-12. This embodiment is similar to the alternate embodiment shown in FIGS. 7-9, except the body 24 has an opening viewable from a side of the band rather than from the top, or plan view. A side 26 of the body is fastened to the band 10 with a fastener 42. Again, detents may be added as desired. A user may rotate the body 10 180 degrees from a desired alignment of the channel if use of a corded tool favors having the opening 32 in a different location based on a technician's experience or preference. For example, if a technician prefers to have a cord hang closer to their hand, as opposed to elbow, the technician may want the opening 32 to face the technician during use of the corded instrument. A technician may want to rotate the body 180 degrees if there is a preference towards draping the cord over the technician's forearm.

While a preferred form of the invention has been shown and described, it will be realized that alterations and modifications may be made thereto without departing from the scope of the following claims.

What is claimed is:

1. A method for positioning a cord of a corded instrument, comprising the steps of:
    securing a band of a cord positioner to a wrist portion of an arm of a technician, said arm being used by the technician to perform a procedure using a corded instrument;
    attaching a cord, which supplies a power source to the corded instrument, to a body fastened to the band such that an instrument end of the cord positioner is nearest a radial aspect of the wrist, and a power source end of the corded instrument enters the cord positioner near an ulnar aspect of the wrist; and
    positioning the cord away from a procedure being performed by the technician by manipulating the position of the cord positioner rather than by touching the cord with a free hand.

2. The method of claim 1 further comprising the steps of removing and discarding the body after the technician has performed the procedure.

3. The method of claim 1 wherein the step of securing is characterized by wrapping the band around a wrist portion of the arm that is holding the corded instrument.

4. The method of claim 1 wherein the power source is air or water.

5. The method of claim 1 wherein the step of attaching is characterized by pushing the cord against cord-holding portions that define an opening until the cord settles into a channel of the body.

6. The method of claim 1 wherein the band is a wearable device that keeps time.

7. The method of claim 1 wherein the body is flexible and rotates relative to the band.

8. The method of claim 1 wherein the step of fastening is further characterized by aligning a detent between the body and the band into a desired position; wherein said desired position is substantially maintained by the detent.

9. A cord positioner usable by a technician comprising:
    a wrist band characterized by a loop-end and a connector end;
    a body fixed to the wrist band between the loop-end and the connector end;
    a channel in the body having an opening that is defined by two cord-holding portions;
    a first side and a second side on either side of the body that are raised relative to a plane defined by the wrist band when it is laying flat;
    a base at a bottom portion of the body that is less flexible than the wrist band because the base is supported by the sides; and
    wherein when in use by the technician, a cord held by the cord-holding portions positions an instrument end of the cord nearest a radial aspect of a technician's wrist, and wherein a power supply end of the cord enters the cord positioner near the ulnar aspect of the technician's wrist such that the technician can hold a corded instrument like a writing instrument and manipulate the cord of the corded instrument by manipulating the wrist band when moving said wrist.

10. The cord positioner of claim 9 further comprising buttresses on either side of the sides, the buttresses providing strength and support to the sides such that the cord-holding portions are more rigid.

11. The cord positioner of claim 9 wherein the channel is aligned with a length of the wrist band.

12. The cord positioner of claim 9 wherein the the cord carries air or water that functions as a power supply for the corded instrument.

13. The cord positioner of claim 9 further comprising reliefs in the sides inside the channels and near the cord-holding portions.

14. The cord positioner of claim 9 further comprising a snap connector near the connector end and a loop near the loop-end; and wherein the snap connector passes through the loop-end so that it can be connected to an adjustment hole.

15. The cord positioner of claim 9 further comprising a sleeve installed into the channel such that smaller diameter cord will not slip easily.

16. The method of claim 3 further comprising the step of the technician repositioning the cord by moving the wrist holding the corded instrument while performing a procedure using the corded instrument.

17. A cord positioner used by a technician comprising:
    a means for attaching a cord of a corded instrument being held by an arm of a technician to said arm of the technician such that the technician can maneuver a position of the cord by just moving said arm;
    wherein the means for attaching positions an instrument end of the cord near a radial aspect of a technician's wrist such that the technician can hold the corded instrument like a writing instrument.

18. The cord positioner of claim 17 characterized by a strap for strapping the cord positioner to a wrist portion of the arm of the technician.

19. The cord positioner of claim 17 wherein the cord delivers air or water to the corded instrument.

20. The cord positioner of claim 18 further comprising a means for securing the cord into the cord positioner.

* * * * *